US00PP29101P2

(12) United States Plant Patent
Berry

(10) Patent No.: US PP29,101 P2
(45) Date of Patent: Mar. 13, 2018

(54) ***RHAPHIOLEPIS* PLANT NAMED 'PS-2013-2'**

(50) Latin Name: *Rhaphiolepis indica*
Varietal Denomination: PS-2013-2

(71) Applicant: Capstone Plants Inc., Grand Saline, TX (US)

(72) Inventor: James B. Berry, Edgewood, TX (US)

(73) Assignee: CAPSTONE PLANTS INC., Grand Saline, TX (US)

( * ) Notice: Subject to any disclaimer, the term of this patent is extended or adjusted under 35 U.S.C. 154(b) by 0 days.

(21) Appl. No.: 15/330,253

(22) Filed: Aug. 30, 2016

(51) Int. Cl.
*A01H 5/02* (2006.01)

(52) U.S. Cl.
USPC ..... Plt./254

(58) Field of Classification Search
USPC ..... Plt./254
See application file for complete search history.

*Primary Examiner* — Anne M Grunberg
(74) *Attorney, Agent, or Firm* — Penny J. Aguirre

(57) ABSTRACT

A new cultivar of *Rhaphiolepis indica* plant named, 'PS-2013-2', that is characterized by its spreading plant habit that is wider than it is tall, its dense self-branching plant habit with short internode lengths, its leather-like leaves that are deep emerald green in color, its flowers that are soft pink in color, its resistance to foliar pathogens, and its foliage and flower buds that are cold hardy at least to U.S.D.A. Zone 7.

2 Drawing Sheets

Botanical classification: *Rhaphiolepis indica.*
Variety denomination: 'PS-2013-2'.

BACKGROUND OF THE INVENTION

The present invention relates to a new and distinct cultivar of *Rhaphiolepis indica* and will be referred to hereafter by its cultivar name, 'PS-2013-2'. 'PS-2013-2' is an evergreen shrub grown for use as a landscape plant and container plantings.

The new cultivar was derived from a controlled breeding program conducted by the Inventor in Grand Saline, Tex. The overall purpose of the breeding program is to develop new cultivars of *Rhaphiolepis* plants with compact growth habits, uniform flowering habits, and glossy, green, disease resistant foliage.

'PS-2013-2' originated from the open pollination of *Rhaphiolepis indica* 'Conor' (U.S. Plant Pat. No. 9,398) in April of 2011. The male parentage is therefore unknown. The collected seeds were treated with the chemical colchicine prior to planting and polyploidy is suspected based on its characteristics but not verified. 'PS-2013-2' was selected as a single unique plant in April of 2013 from amongst the resulting seedlings.

Asexual propagation of the new cultivar was first accomplished by the Inventor by semi-hardwood stern cuttings in June of 2013 in Grand Saline, Tex. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PS-2013-2' as a unique cultivar of *Rhaphiolepis.*

1. 'PS-2013-2' exhibits a spreading plant habit that is wider than it is tall.

2. 'PS-2013-2' exhibits a dense self-branching plant habit with short internode lengths.
3. 'PS-2013-2' exhibits leather-like leaves that are deep emerald green in color.
4. 'PS-2013-2' exhibits flowers that are soft pink in color.
5. 'PS 2013-2' exhibits resistance to foliar pathogens.
6. 'PS-2013-2' exhibits foliage and flower buds that are cold hardy at least to U.S.D.A. Zone 7.

The female parent of 'PS-2013-2', 'Conor', differs from 'PS-2013-2' in having a plant habit that is equal in height and width, in being less well-branched, in having foliage that is olive green in color, and in having flowers that are darker pink in color. 'PS-2013-2' can be most closely compared to the *Rhaphiolepis indica* cultivars 'Hines Darkleaf' (U.S. Plant Pat. No. 8,635) and 'Sopink' (U.S. Plant Pat. No. 14,388). 'Hines Darkleaf' is similar to 'PS-2013-2' in having foliage that is deep green in color and in having leaves with a leathery texture. 'Hines Darkleaf' differs from 'PS-2013-2' in being less densely branched (not self-branched), in having flowers that are darker pink in color, and in being susceptible to foliar pathogens. 'Sopink' is similar to 'PS-2013-2' in being resistant to foliar pathogens and in having flowers that are soft pink in color. 'Sopink' differs from 'PS-2013-2' in having a mounded plant habit, in having foliage that is dull olive green in color, and in having flowers with petals that are oblanceolate in shape.

BRIEF DESCRIPTION OF THE DRAWINGS

The accompanying colored photographs illustrate the overall appearance and distinct characteristics of the new *Rhaphiolepis*. The plants in the photographs were taken of a plant 2.5 years in age as grown in a two-gallon container outdoors in Grand Saline, Tex.

The photograph in FIG. 1 provides a top view of 'PS-2013-2' in bloom.

Figure 1:
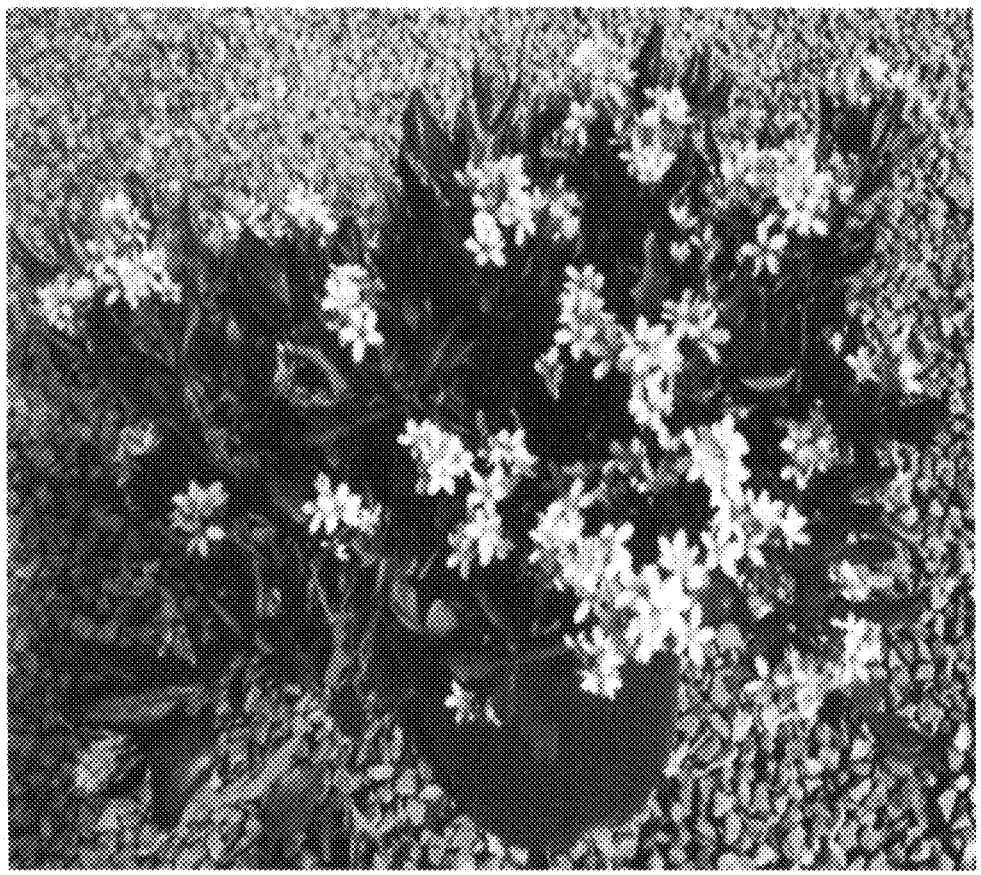
Figure 2:
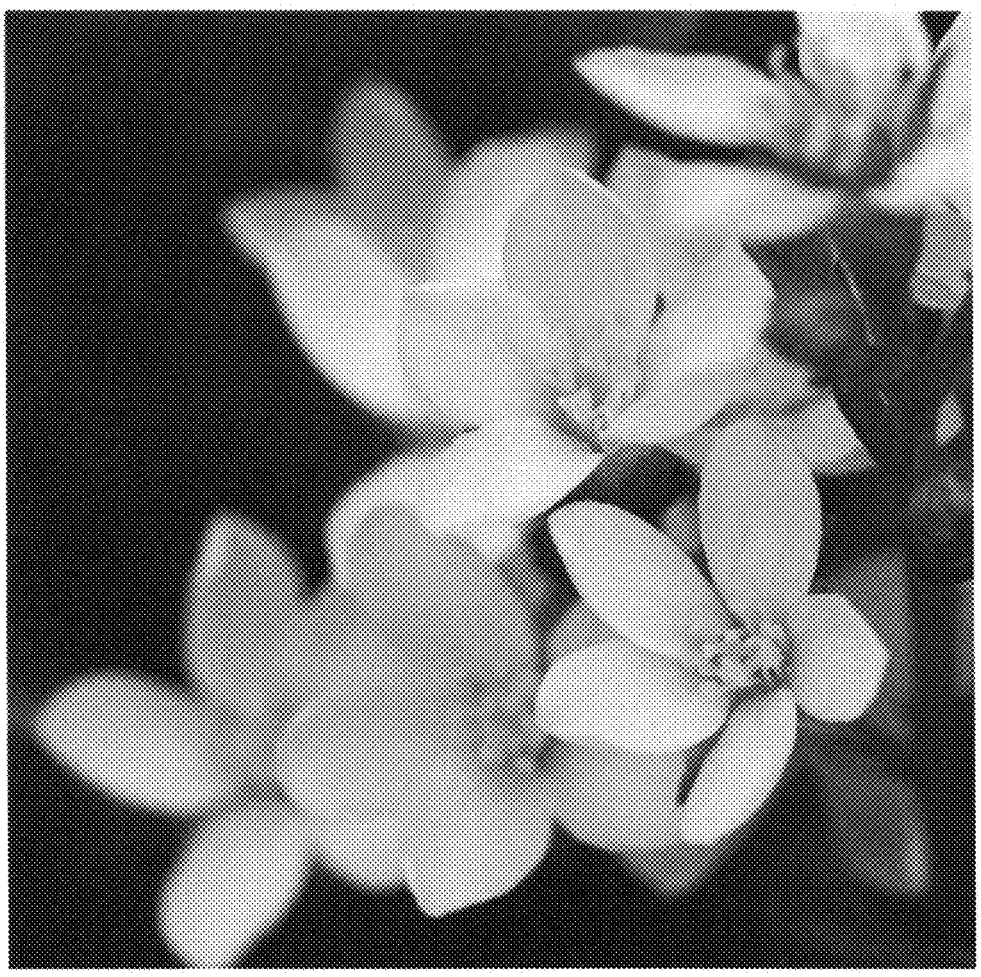

The photograph in FIG. 2 provides a close-up view of the flowers of 'PS-2013-2'.

The colors in the photographs are as close as possible with the digital photography techniques available and the color values cited in the detailed botanical description accurately describe the colors of the new *Rhaphiolepis*.

DETAILED BOTANICAL DESCRIPTION

The following is a detailed description of 2.5 year-old plants of the new cultivar as grown outdoors in 2-gallon containers in Grande Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—For three weeks in April in Grand Saline, Tex.

*Plant type*.—Evergreen shrub.

*Plant habit*.—Well-branched and spreading wider than tall.

*Height and spread*.—Reaches an average of 0.6 m in height and 1.2 m in spread.

*Cold hardiness*.—At least to U.S.D.A. Zone 7.

*Diseases/pests*.—Resistance to foliar diseases caused by the pathogens *Colletotrichum* spp, *Botryosphaeria corticola, Cercospora* spp., and *Entomosporium maculatum* has been observed.

*Root description*.—Fibrous and fine, 175A in color.

*Root initiation*.—An average of four weeks for root initiation with a rooted cutting produced after 12 weeks.

*Root development*.—About 24 months to fully root in a 3-gallon container.

*Propagation*.—Semi-hardwood stem cuttings.

*Growth rate*.—Moderate.

Stem description:

*Shape*.—Round.

*Stem quantity*.—Main stems; an average of 11, lateral branches; up to 15 branches per main stem.

*Stem color*.—A blend between 202B to 202C and N200A.

*Stem size*.—Main stems; an average of 15 cm in length and 5 mm in width, lateral stems; an average of 5 cm in length and 4 mm in width.

*Stem surface*.—Rugose, woody and bark-like.

*Internode length*.—Varies in length, an average of 3 cm.

*Branching*.—Densely branched with branches growing outward, semi-erect and ascending.

Foliage description:

*Leaf shape*.—Elliptic.

*Leaf division*.—Simple.

*Leaf base*.—Acute.

*Leaf apex*.—Round.

*Leaf fragrance*.—None.

*Leaf venation*.—Pinnate, upper surface; N144A, main vein more prominent, lower surface; main vein more prominent and N144A, other veins 137A.

*Leaf margins*.—Entire.

*Leaf arrangement*.—Opposite along the branch and whorled at the base of the inflorescence.

*Leaf quantity*.—An average of 35 leaves per lateral branch.

*Leaf attachment*.—Petiolate.

*Leaf substance*.—Moderately thick (leather-like) and strong.

*Leaf surface*.—Newly expanded leaves; upper surface glossy and lower surface dull, mature upper surface; semi-glossy and leathery and lower surface; dull.

*Leaf size*.—An average of 6 cm in length and 2.5 cm in width.

*Leaf color*.—Newly expanded leaves; upper surface a blend between NN137A and 144A and flushed with 184A mainly on the veins and margins, lower surface 131A, mature leaves; upper surface 131A, lower surface 144A.

*Petiole*.—An average of 1 cm in length and 2 mm in width, color; 145B, occasionally flushed with 174A to 175A, strong, glabrous and semi-glossy surface.

Inflorescence description:

*Inflorescence type*.—Terminal compound corymb.

*Inflorescence size*.—An average of 10 cm in length and 5 cm in width.

*Flower buds*.—Lanceolate in shape, an average of 9 mm in length and 3 mm in width, a blend of 144A and N144A, flushed with 59A and 187A at the apex and closed bud margins, surface is slightly glossy and covered with short pubescent hairs, color of hairs varies between matching the surface color of the bud, 164A, and 161A and are less than 0.5 mm in length.

*Flower fragrance*.—Slight pleasant fragrance.

*Flower and bud quantity*.—An average of 20 per peduncle.

*Flower type*.—Rotate with slightly cupped petals and prominent stamens and ovary.

*Flower aspect*.—Upwards.

*Flower lastingness*.—About 10 days.

*Flower size*.—An average of 2 cm in diameter and 1 cm in depth.

*Petals*.—5, elliptical in shape, angle of petals ranges between horizontal and slightly upright with a slightly cupped form, about 2 mm of base is fused into calyx that is apiculate in shape, ranging between rounded to tri-notched apex, entire margins, upper and lower surfaces are glabrous and satiny, an average of 8 mm in length and 6 mm in width, color: upper and lower surfaces when opening and when fully open; a blend between 69D, 75C and N74B to N74D with base NN155D.

*Calyx*.—Calyx portion is wrapped around petals when in bud and reflexed on mature flowers with un-fused sepals, about 1 cm in diameter and 2 mm in depth.

*Sepals*.—5, an average of 3 mm in length and 2 mm in width, triangular in shape, acute apex, truncate base, margins are entire and densely covered with woolly pubescence 158A in color and up to 1 mm in length, upper (inner) and lower (outer) surface color is a blend of144A and N144A flushed with 59A and 187A at the tips, upper (inner) surface is glossy and glabrous, lower (outer) surface is slightly glossy and moderately covered with short pubescent hairs that match the surface color and are less than 0.5 mm in length.

*Peduncles*.—An average of 2 cm in length and 3 mm in width, 145A to 146A in color and slightly flushed with 176A at the nodes, slightly glossy surface, lightly covered with fine short pubescence that varies between matching the surface color and 176A, less than 0.5 mm in length, strong.

*Pedicels*.—An average of 5 mm in length and 2 mm in width, a mix of 145A to 146A in color and slightly flushed with 176A, slightly glossy surface, lightly covered with fine short pubescence that varies between matching the surface color and 176A, less than 0.5 mm in length, strong.

*Bracts*.—Bracts emerge at the base of a corymb and form a whorl of up to 10, an average of 6 mm in length and 3 mm in width, triangular in shape, acute to acuminate apex, outer color is a blend of 144A and N144A, flushed with 59A and 187A, inner color is a blend between163B and 190A, outer surface is glossy, inner surface is dull.

*Bracteole*.—An average of 2 per pedicel, an average of 6 mm in length and 1 mm in width, color varies between 144A and N144A.

Reproductive organs:

*Gynoecium*.—Pistil; 2, an average of 9 mm in length and 0.5 mm in width, stigma; 142C in color, 0.5 mm in diameter, and rounded in shape, style; 142C in color and an average of 8.5 mm in length and 0.5 mm in width, ovary; round, 145D in color, 2 mm in diameter.

*Androecium*.—Stamens; about 15, an average of 6 mm in length, filaments; NN155D in color, an average of 5 mm in length and 0.5 mm in width, anthers; 11A in color, club shaped, an average of 1 mm in length and width, no pollen observed.

*Fruit/seeds*.—Fruit; globose in shape, 144B in color and becomes suffused with 178A, an average of 7.5 mm in length and width, seed; 1, globose nut, an average of 6 mm in length and width, 158A in color.

It is claimed:

1. A new and distinct cultivar of *Rhaphiolepis* plant named 'PS-2013-2' as herein illustrated and described.

* * * * *